US009646395B2

(12) United States Patent
Ben-Oni et al.

(10) Patent No.: US 9,646,395 B2
(45) Date of Patent: May 9, 2017

(54) METHOD AND APPARATUS FOR COMPARING PORTIONS OF A WAVEFORM

(71) Applicant: McKesson Financial Holdings, Hamilton (BM)

(72) Inventors: Elan Ben-Oni, El Cerrito, CA (US); Michael J. Pecora, Pittsburgh, PA (US)

(73) Assignee: Change Healthcare LLC, Alpharetta, GA (US)

( * ) Notice: Subject to any disclaimer, the term of this patent is extended or adjusted under 35 U.S.C. 154(b) by 409 days.

(21) Appl. No.: 14/192,242

(22) Filed: Feb. 27, 2014

(65) Prior Publication Data

US 2015/0243040 A1 Aug. 27, 2015

(51) Int. Cl.
*G06T 11/20* (2006.01)
*A61B 5/00* (2006.01)
*A61B 5/0402* (2006.01)

(52) U.S. Cl.
CPC ........... *G06T 11/206* (2013.01); *A61B 5/0006* (2013.01); *A61B 5/0402* (2013.01); *A61B 5/742* (2013.01)

(58) Field of Classification Search
USPC .......................................................... 345/629
See application file for complete search history.

(56) References Cited

U.S. PATENT DOCUMENTS

| | | | | |
|---|---|---|---|---|
| 5,042,077 A * | 8/1991 | Burke | ................... | G01R 33/54 382/128 |
| 5,284,152 A * | 2/1994 | Portnuff | .............. | G06F 19/3406 600/525 |
| 5,579,463 A | 11/1996 | Takano et al. | | |
| 5,611,060 A * | 3/1997 | Belfiore | ................ | G06F 3/0485 715/819 |
| 8,478,393 B2 | 7/2013 | Ramanathan et al. | | |
| 8,620,418 B1 | 12/2013 | Kuppuraj et al. | | |
| 2002/0062199 A1 | 5/2002 | Pickerd et al. | | |
| 2004/0164984 A1 | 8/2004 | Pickerd | | |
| 2004/0183818 A1* | 9/2004 | Beasley | ................ | G06F 3/0481 345/660 |

(Continued)

FOREIGN PATENT DOCUMENTS

JP 2010054318 3/2010
WO WO 2015/107635 A1 7/2015

OTHER PUBLICATIONS

Examination Report for Australian Application No. 2015200996 dated Nov. 20, 2015.

(Continued)

*Primary Examiner* — Kimbinh T Nguyen
(74) *Attorney, Agent, or Firm* — Alston & Bird LLP

(57) ABSTRACT

A method, apparatus and computer program product are therefore provided in order to provide for display of waveforms. An example method may include displaying a first waveform, receiving an input selecting a portion of the first waveform, and generating, using a processor, an interface control displaying the selected portion of the first waveform. The interface control may include a semi-transparent display area and the selected portion of the first waveform may be displayed on the semi-transparent display area. The method may also include displaying the interface control concurrently with a second waveform such that at least a portion of the second waveform is visible through the semi-transparent display area of the interface control.

19 Claims, 6 Drawing Sheets

(56) References Cited

U.S. PATENT DOCUMENTS

| | | |
|---|---|---|
| 2005/0027201 A1 | 2/2005 | Badilini et al. |
| 2007/0010753 A1 | 1/2007 | MacAdam |
| 2008/0281168 A1 | 11/2008 | Gibson et al. |
| 2009/0054743 A1 | 2/2009 | Stewart |
| 2009/0069704 A1* | 3/2009 | MacAdam ............. A61B 5/044 600/523 |
| 2010/0056128 A1 | 3/2010 | Hwang et al. |
| 2010/0214296 A1 | 8/2010 | Kawamura |
| 2010/0265253 A1 | 10/2010 | Li |
| 2011/0071414 A1 | 3/2011 | Heil et al. |
| 2011/0074788 A1* | 3/2011 | Regan ................. G06F 19/3406 345/440 |
| 2011/0172505 A1 | 7/2011 | Kim et al. |
| 2012/0171650 A1 | 7/2012 | Warner et al. |
| 2012/0278099 A1 | 11/2012 | Kelly et al. |
| 2013/0046149 A1 | 2/2013 | Gettelman et al. |
| 2014/0125600 A1 | 5/2014 | Meng et al. |
| 2014/0243612 A1 | 8/2014 | Li et al. |
| 2014/0275819 A1 | 9/2014 | Kassem et al. |
| 2014/0276140 A1 | 9/2014 | Kinghorn |
| 2014/0330146 A1 | 11/2014 | Kuppuraj et al. |
| 2014/0351738 A1 | 11/2014 | Kokovidis et al. |
| 2015/0248534 A1 | 9/2015 | Krzywicki et al. |

OTHER PUBLICATIONS

Office Action for U.S. Appl. No. 14/184,076 dated Dec. 30, 2015.
Office Action for U.S. Appl. No. 14/183,998 dated Dec. 30, 2015.
Combined Search and Examination Report for Application No. GB1503352.5 dated Aug. 27, 2015.
Office Action for U.S. Appl. No. 14/183,998 dated Jun. 4, 2015.
Office Action for U.S. Appl. No. 14/184,076 dated Jun. 9, 2015.
U.S. Appl. No. 14/183,998, filed Feb. 19, 2014, In re: Ben-Oni entitled *Method and Apparatus for Displaying One or More Waveforms*.
U.S. Appl. No. 14/184,076, filed Feb. 19, 2014, In re: Ben-Oni entitled *Method and Apparatus for Displaying One or More Waveforms*.
Office Action for U.S. Appl. No. 14/183,998 dated Jul. 27, 2016.
Office Action for U.S. Appl. No. 14/184,076 dated Jun. 16, 2016.
Office Action for U.S. Appl. No. 14/184,076 dated Sep. 28, 2016.

* cited by examiner

METHOD AND APPARATUS FOR COMPARING PORTIONS OF A WAVEFORM

TECHNOLOGICAL FIELD

An example embodiment of the present invention relates generally to electrocardiogram displays, and, more particularly, to a method and apparatus for displaying one or more electrocardiogram waveforms.

BACKGROUND

Recent trends in technology have provided for increased interoperability between devices. As computing devices have become more powerful, it is increasingly common for mobile devices to be used in roles that were formerly the domain of desktop and mainframe computers. Users are frequently able to employ smart phones and tablet computers to perform tasks that previously would have required bulky displays and hardware enclosures. One technological field in particular that has benefited from these advancements is that of medical diagnostics.

Medical diagnostic devices have traditionally required special purpose hardware and software to analyze diagnostic sensor input. Display and analysis equipment might, at best, be attached to a cart structure that provided portability throughout different parts of a medical facility. However, the proliferation of mobile devices such as tablets computers, netbooks, and smart phones has provided practitioners with lightweight, portable devices that also possess detailed displays and significant processing power. Some manufacturers have leveraged these mobile devices via display and analysis applications to eliminate the need for specialized display and analysis hardware for analyzing medical diagnostic data.

However, the use of these mobile devices also presents new challenges compared to the specially designed display and analysis equipment of the past. Mobile devices may have a constrained display area, making fine measurements and calibrations of data difficult. Limited display areas may seem cluttered and input operations may be difficult due to the low input resolution of some touch screen displays. These problems are particularly pronounced in scenarios where a practitioner is comparing two or more sets of data. For example, analysis of electrocardiogram (ECG) waveforms typically involves comparison of a previously captured waveform with a newly captured waveform in order to note any differences between the old waveform and the new waveform. Simultaneous display of both waveforms may require condensing of the display interface, making it difficult to analyze both waveforms at once. Similarly, it is difficult to compare sections of a waveform within a single waveform. Through applied effort, ingenuity, and innovation, Applicant has solved many of these identified problems by developing a solution that is embodied by the present invention, which is described in detail below

BRIEF SUMMARY

A method, apparatus and computer program product are therefore provided according to an example embodiment of the present invention in order to provide improved methods, apparatuses, and computer program products for comparing portions of a waveform. An example embodiment of a method may include displaying a first waveform, receiving an input selecting a portion of the first waveform, and generating, using a processor, an interface control displaying the selected portion of the first waveform. The interface control may include a semi-transparent display area and the selected portion of the first waveform may be displayed on the semi-transparent display area. The method may further include displaying the interface control concurrently with a second waveform such that at least a portion of the second waveform is visible through the semi-transparent display area of the interface control.

Example embodiments may also include an apparatus. The apparatus may include processing circuitry configured to cause the apparatus to perform certain actions. The apparatus may be caused to display a first waveform, receive an input selecting a portion of the first waveform, and generate an interface control displaying the selected portion of the first waveform. The interface control may include a semi-transparent display area and the selected portion of the first waveform may be displayed on the semi-transparent display area. The apparatus may also be caused to display the interface control concurrently with a second waveform such that at least a portion of the second waveform is visible through the semi-transparent display area of the interface control.

Additional embodiments may include a computer program product. The computer program product may include at least one computer-readable storage medium bearing computer program instructions embodied therein for use with a computer. The computer program instructions may include program instructions configured to display a first waveform, receive an input selecting a portion of the first waveform, and generate an interface control displaying the selected portion of the first waveform. The interface control may include a semi-transparent display area and the selected portion of the first waveform may be displayed on the semi-transparent display area. The program instructions may also display the interface control concurrently with a second waveform such that at least a portion of the second waveform is visible through the semi-transparent display area of the interface control.

The above summary is provided merely for purposes of summarizing some example embodiments to provide a basic understanding of some aspects of the invention. Accordingly, it will be appreciated that the above-described embodiments are merely examples and should not be construed to narrow the scope or spirit of the invention in any way. It will be appreciated that the scope of the invention encompasses many potential embodiments in addition to those here summarized, some of which will be further described below.

BRIEF DESCRIPTION OF THE DRAWINGS

Figure 1:
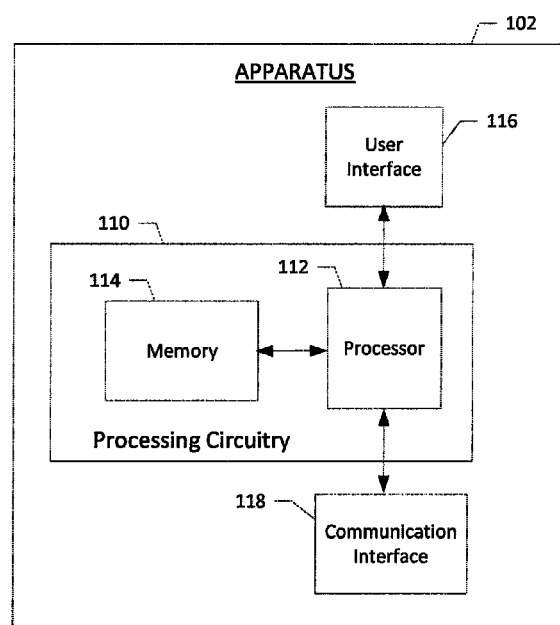
Figure 2:
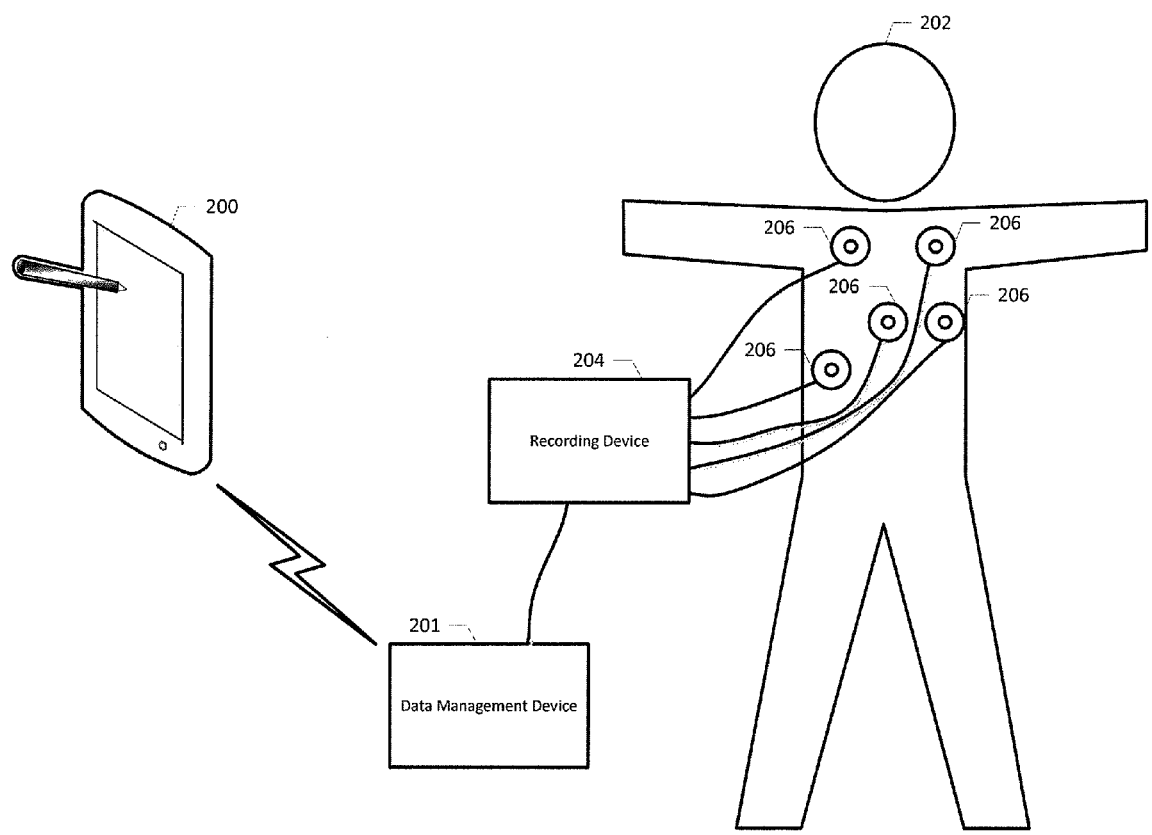
Figure 3:
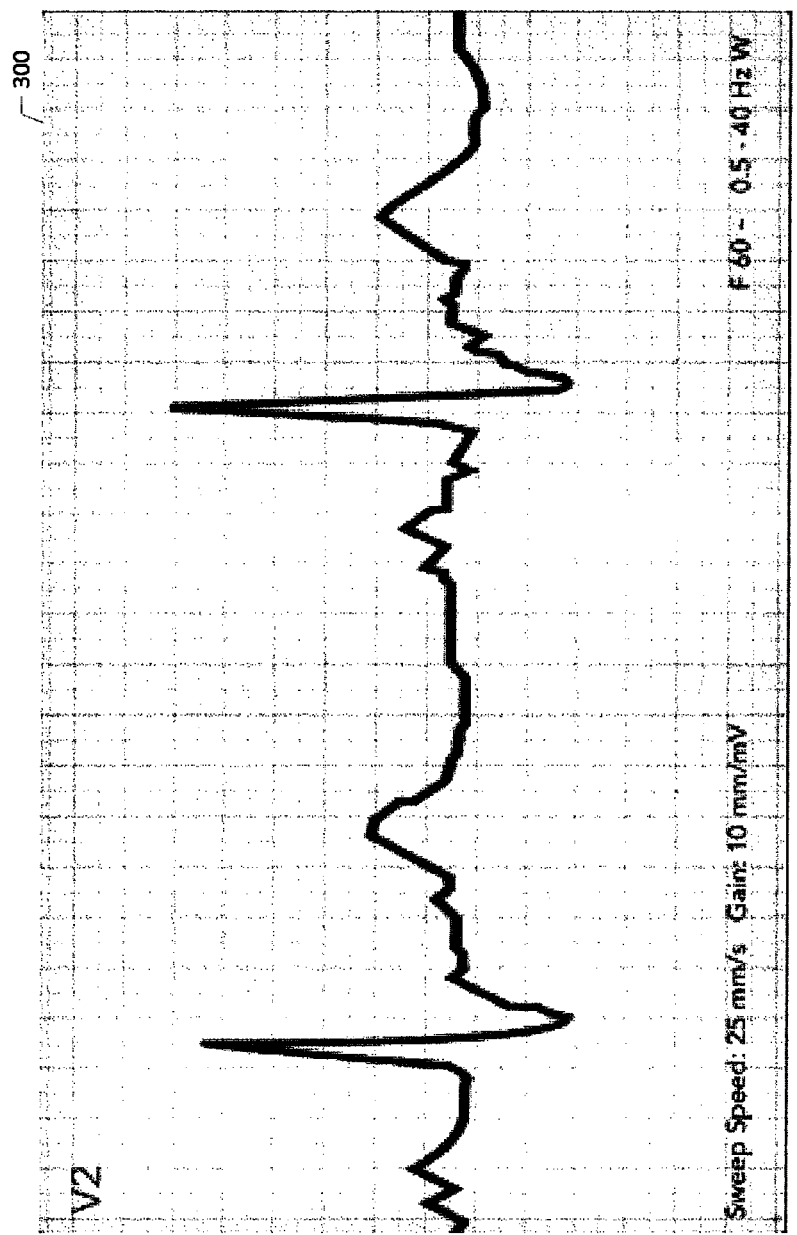
Figure 4:
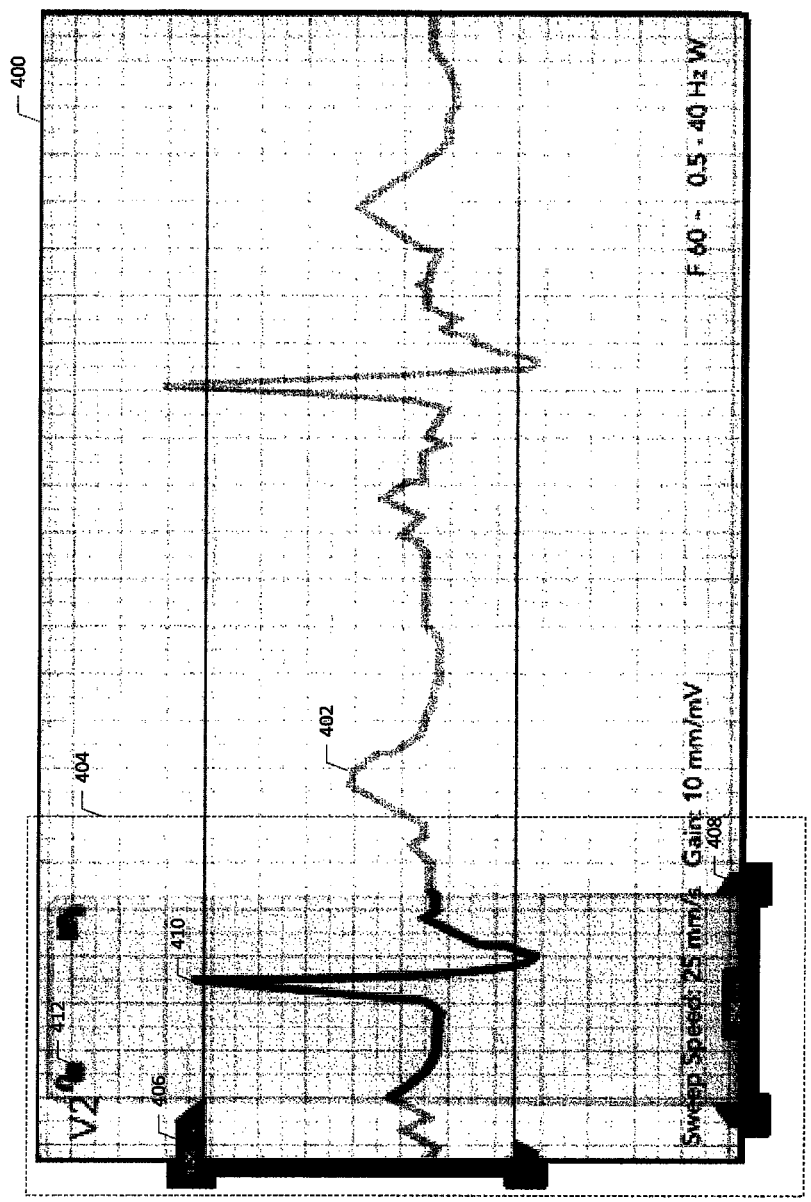
Figure 5:
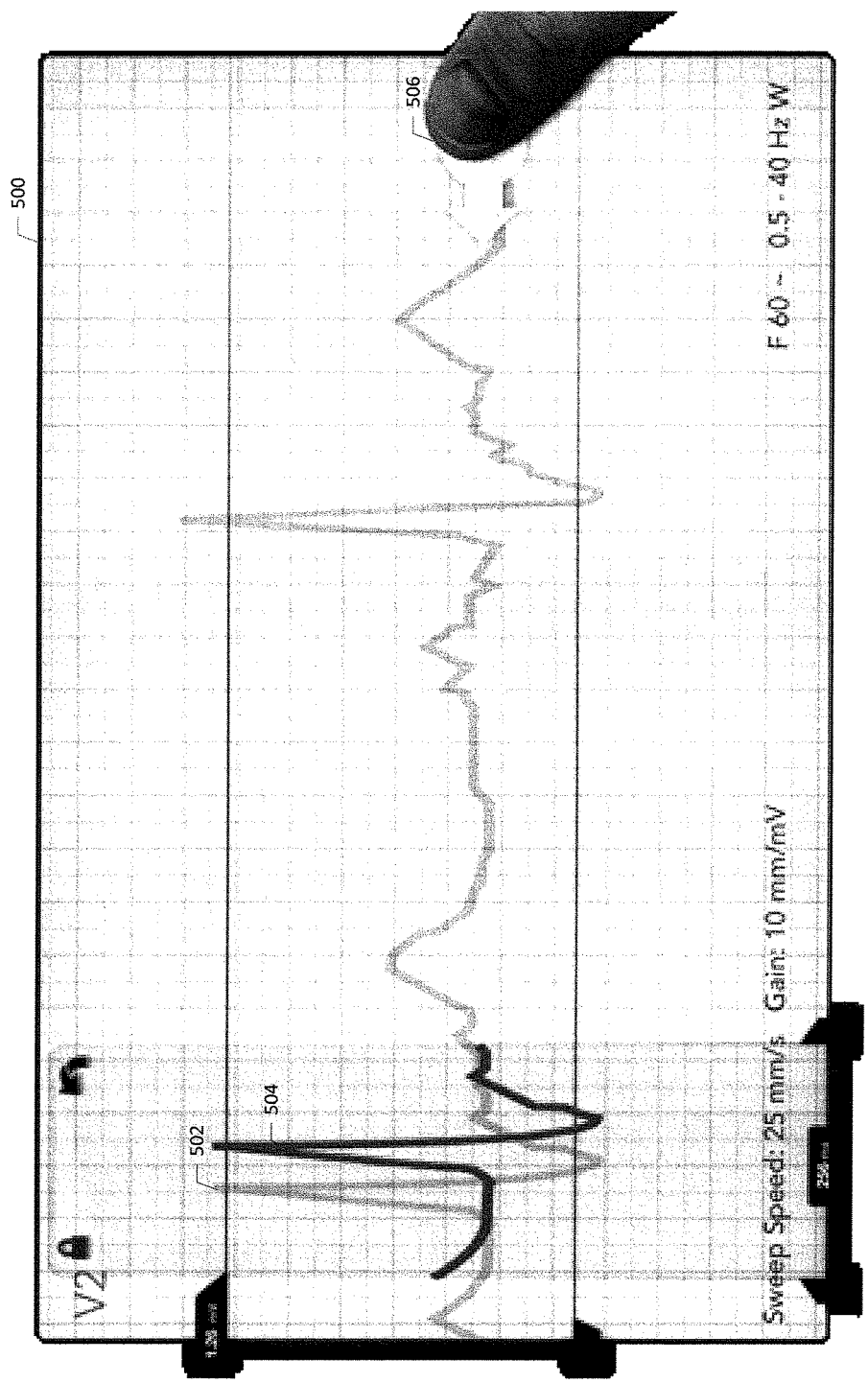
Figure 6:
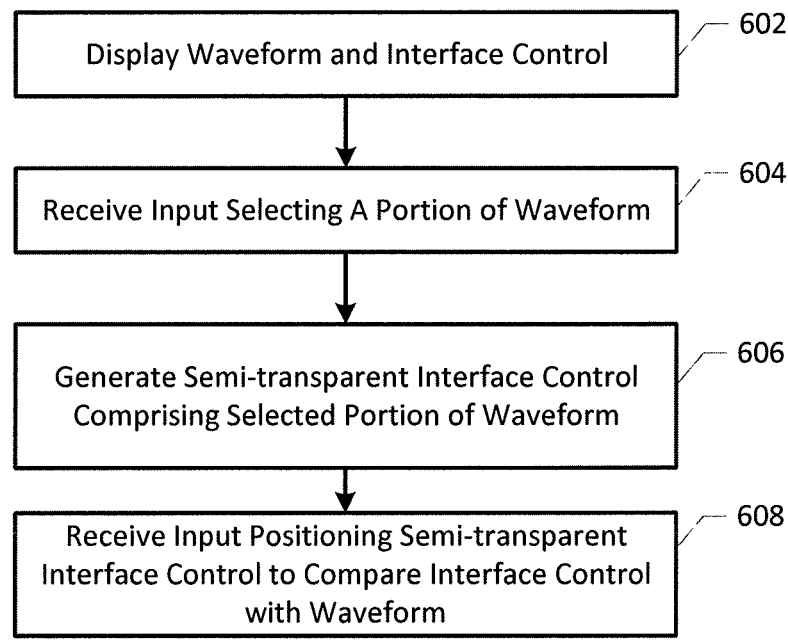

Having thus described certain embodiments of the invention in general terms, reference will now be made to the accompanying drawings, which are not necessarily drawn to scale, and wherein:

FIG. 1 is a block diagram of an apparatus that may be specifically configured in accordance with example embodiments of the present invention;

FIG. 2 is a functional diagram depicting an example apparatus in communication with a medical diagnostic device in accordance with example embodiments of the present invention;

FIG. 3 is an illustration of an example user interface for displaying a waveform in accordance with example embodiments of the present invention;

FIG. 4 is an illustration of an example user interface for displaying an interface control used to select at least a portion of a waveform in accordance with example embodiments of the present invention;

FIG. 5 is an illustration of an example user interface for using an interface control to compare a selected portion of a waveform with the same or another waveform in accordance with example embodiments of the present invention; and FIG. 6 is a flow diagram of an example method for analyzing a waveform using an interface control in accordance with embodiments of the present invention.

DETAILED DESCRIPTION

The present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Introduction and Definitions

A method, apparatus and computer program product are provided in accordance with an example embodiment of the present invention in order to display and compare waveforms. In this regard, a method, apparatus and computer program product of an example embodiment may receive waveform data. The waveform data may include two or more waveforms. These waveforms may correspond to readings taken for a particular patient using a waveform measurement device, such as an electrocardiograph or an electroencephalograph. Embodiments may format this waveform data in a manner that facilitates comparison of two separate waveforms, such as a first waveform from a previous measurement (e.g., a "known good" measurement) in the patient's medical history, and a second waveform captured at a later time. Comparison between the waveforms may be provided on a display screen, such as a display coupled to a smartphone or tablet computer. Embodiments may provide various ways of formatting and displaying these waveforms to facilitate comparison and leverage the use of a particular display and input devices. For example, embodiments may leverage features of touch screen input devices to improve the ability of practitioners to align waveforms.

Embodiments may facilitate waveform comparison operations by providing an interface control allowing for capturing of a portion of the waveform. The interface control may display the captured portion of the waveform in a semi-transparent manner such that the captured waveform may be superimposed upon another waveform or another portion of the same waveform such that both the captured waveform and another waveform or another portion of the same waveform are visible. The interface control may be represented as a scrolling caliper, with horizontal and/or vertical interface control elements for defining the selected portion of the waveform to be displayed in the interface control.

For the purposes of this application, the teem "waveform information" should be understood to refer to information provided by medical diagnostic devices, including but not necessarily limited to electrocardiogram waveforms or electroencephalograph waveforms. Said waveform information may also include metadata describing the waveform (e.g., measurements from a series of leads affixed to a patient), the diagnostic device used to capture the waveform, the time, date, or facility in which the waveform was captured, the patient associated with the waveform, or the like. A given waveform may include measurements from a plurality of sensors. For example, a waveform may include measurements from multiple leads of an electrocardiograph (e.g., information received from Lead I, Lead II, Lead II, Lead aVR, Lead aVL, Lead aVF, and Leads V1-V6 of a 12 lead electrocardiogram). As such, the term "waveform" should be understood to refer to a particular set of readings from an example device, such that a single waveform may encompass multiple sensor readings. The waveform information may include a plurality of waveforms. For example, a given set of waveform information may include data describing all waveforms captured for a particular patient over the patient's medical history. Alternatively, waveform information may include a single waveform captured during a single diagnostic operation.

For the purposes of this application, the term "medical diagnostic device" should be understood to refer to a device or combination of devices that is equipped and/or configured to capture and/or display patient diagnostic data, such as waveform information. For example, a medical diagnostic device may include a monitor (e.g., a "Holter" electrocardiograph device) that measures and stores patient waveform information for later analysis. In other embodiments, a medical diagnostic device may include a specially configured computer for analyzing waveform information. For example, a medical diagnostic device may include a smartphone, laptop, or tablet computer programmed for display and analysis of waveform information. As yet another example, a medical diagnostic device may include both a sensor device (e.g., a device for measuring waveform information and transmitting the information) and an analysis device (e.g., a computer for analyzing and displaying waveform information received from the sensor device).

For the purposes of this application, the term "semi-transparent," as described in the context of a semi-transparent interface control, should be understood to refer to a visible portion of an interface element that displays one or more visible elements (e.g., waveforms) while not obscuring one or more visible elements disposed behind or underneath the semi-transparent interface control. In some embodiments, the portions of the interface elements that correspond to the displayed visible elements may be opaque, while the remainder of the interface element is semi-transparent. For example, a first waveform displayed on a semi-transparent display area may be opaque while the remainder of the semi-transparent display area allows for viewing of a second waveform disposed behind the semi-transparent display area, thus allowing a comparison between the first waveform and the second waveform. It should be appreciated that an example interface control may include both semi-transparent and opaque elements. For example, an interface control might include both a transparent display area and one or more opaque control elements for moving the transparent display area or altering the dimensions of the transparent display area.

Example Apparatus

FIG. 1 illustrates a block diagram of an apparatus 102 in accordance with some example embodiments. The apparatus 102 may be any computing device capable of facilitating viewing and analysis of waveform information as described herein. For example, the apparatus 102 may be implemented on a smart phone, personal digital assistant, tablet computer, netbook computer, laptop, or desktop. The apparatus 102 may be operable to display waveform information to a user, and to facilitate the comparison of multiple waveforms. Accordingly, it will be appreciated that the apparatus 102 may comprise an apparatus configured to implement and/or otherwise support implementation of various example embodiments described herein.

It should be noted that the components, devices or elements illustrated in and described with respect to FIG. 1 below may not be mandatory and thus some may be omitted in certain embodiments. Additionally, some embodiments may include further or different components, devices or elements beyond those illustrated in and described with respect to FIG. 1.

The apparatus 102 may include or otherwise be in communication with processing circuitry 110 that is configurable to perform actions in accordance with one or more example embodiments disclosed herein. In this regard, the processing circuitry 110 may be configured to perform and/or control performance of one or more functionalities of the apparatus 102 (e.g., functionalities of a computing device on which the apparatus 102 may be implemented) in accordance with various example embodiments, and thus may provide means for performing functionalities of the apparatus 102 (e.g., functionalities of a computing device on which the apparatus 102 may be implemented) in accordance with various example embodiments. The processing circuitry 110 may be configured to perform data processing, application execution and/or other processing and management services according to one or more example embodiments. In some embodiments, the apparatus 102 or a portion(s) or component(s) thereof, such as the processing circuitry 110, may be embodied as or comprise a chip or chip set. In other words, the apparatus 102 or the processing circuitry 110 may comprise one or more physical packages (e.g., chips) including materials, components and/or wires on a structural assembly (e.g., a baseboard). The apparatus 102 or the processing circuitry 110 may therefore, in some cases, be configured to implement an embodiment of the invention on a single chip or as a single "system on a chip." As such, in some cases, a chip or chipset may constitute means for performing one or more operations for providing the functionalities described herein.

In some example embodiments, the processing circuitry 110 may include a processor 112 and, in some embodiments, such as that illustrated in FIG. 1, may further include memory 114. The processing circuitry 110 may be in communication with or otherwise control a user interface 116 and/or a communication interface 118. As such, the processing circuitry 110 may be embodied as a circuit chip (e.g., an integrated circuit chip) configured (e.g., with hardware, software or a combination of hardware and software) to perform operations described herein.

The processor 112 may be embodied in a number of different ways. For example, the processor 112 may be embodied as various processing means such as one or more of a microprocessor or other processing element, a coprocessor, a controller or various other computing or processing devices including integrated circuits such as, for example, an ASIC (application specific integrated circuit), an FPGA (field programmable gate array), or the like. Although illustrated as a single processor, it will be appreciated that the processor 112 may comprise a plurality of processors. The plurality of processors may be in operative communication with each other and may be collectively configured to perform one or more functionalities of the apparatus 102 as described herein. The plurality of processors may be embodied on a single computing device or distributed across a plurality of computing devices collectively configured to function as the apparatus 102. In some example embodiments, the processor 112 may be configured to execute instructions stored in the memory 114 or otherwise accessible to the processor 112. As such, whether configured by hardware or by a combination of hardware and software, the processor 112 may represent an entity (e.g., physically embodied in circuitry—in the form of processing circuitry 110) capable of performing operations according to embodiments of the present invention while configured accordingly. Thus, for example, when the processor 112 is embodied as an ASIC, FPGA or the like, the processor 112 may be specifically configured hardware for conducting the operations described herein. Alternatively, as another example, when the processor 112 is embodied as an executor of software instructions, the instructions may specifically configure the processor 112 to perform one or more operations described herein.

In some example embodiments, the memory 114 may include one or more non-transitory memory devices such as, for example, volatile and/or non-volatile memory that may be either fixed or removable. In this regard, the memory 114 may comprise a non-transitory computer-readable storage medium. It will be appreciated that while the memory 114 is illustrated as a single memory, the memory 114 may comprise a plurality of memories. The plurality of memories may be embodied on a single computing device or may be distributed across a plurality of computing devices collectively configured to function as the apparatus 102. The memory 114 may be configured to store information, data, applications, instructions and/or the like for enabling the apparatus 102 to carry out various functions in accordance with one or more example embodiments. For example, the memory 114 may be configured to buffer input data for processing by the processor 112. Additionally or alternatively, the memory 114 may be configured to store instructions for execution by the processor 112. As yet another alternative, the memory 114 may include one or more databases that may store a variety of files, contents or data sets. Among the contents of the memory 114, applications may be stored for execution by the processor 112 in order to carry out the functionality associated with each respective application. In some cases, the memory 114 may be in communication with one or more of the processor 112, user interface 116, or communication interface 118 via a bus or buses for passing information among components of the apparatus 102.

The user interface 116 may be in communication with the processing circuitry 110 to receive an indication of a user input at the user interface 116 and/or to provide an audible, visual, mechanical or other output to the user. As such, the user interface 116 may include, for example, a keyboard, a mouse, a joystick, a display, a touch screen display, a microphone, a speaker, a Light Emitting Diode (LED), a lighting device, an electronic sensor for capturing human body movements, and/or other input/output mechanisms. In some embodiments, the user interface 116 includes a touch screen input device for displaying waveform information. The touch screen input device may facilitate formatting and output of waveform information to assist a practitioner with comparison and analysis of multiple waveforms. Although described with respect to a touch screen, it should also be appreciated that the user interface 116 may be provided via other techniques, such as a display device in concert with a mouse, keyboard, joystick, touchpad, or the like.

The communication interface 118 may include one or more interface mechanisms for enabling communication with other devices and/or networks. In some cases, the communication interface 118 may be any means such as a device or circuitry embodied in either hardware, or a combination of hardware and software that is configured to receive and/or transmit data from/to a network and/or any other device or module in communication with the processing circuitry 110. By way of example, the communication interface 118 may be configured to enable the apparatus 102 to communicate with another computing device via a wireless network, such as a wireless local area network (WLAN), cellular network, and/or the like. Additionally or alternatively, the communication interface 118 may be configured to enable the apparatus 102 to communicate with another computing device via a wireline network. In some example embodiments, the communication interface 118 may be configured to enable communication between the apparatus 102 and one or more further computing devices via the internet. Accordingly, the communication interface 118 may, for example, include an antenna (or multiple antennas) and supporting hardware and/or software for enabling communications with a wireless communication network (e.g., a wireless local area network, cellular network, and/or the like) and/or a communication modem or other hardware/software for supporting communication via cable, digital subscriber line (DSL), universal serial bus (USB), Ethernet or other methods. In some embodiments, the communication interface 118 may be configured to communicate with an external device, such as a sensor device capturing waveform information as described above. Additionally or alternatively, the communication interface 118 may communicate with a remote datastore (e.g., a medical records database) to obtain stored waveform information.

Having now described an apparatus configured to implement and/or support implementation of various example embodiments, features of several example embodiments will now be described. It will be appreciated that the following features are non-limiting examples of features provided by some example embodiments. Further, it will be appreciated that embodiments are contemplated within the scope of disclosure that implement various subsets or combinations of the features further described herein. Accordingly, it will be appreciated that some example embodiments may omit one or more of the following features and/or implement variations of one or more of the following features.

Example Device Architecture

FIG. 2 is a block diagram of a device architecture in accordance with example embodiments of the present invention. The illustration depicts a recording device 204 coupled to a patient 202 in communication with a display device 200 via a data management device 201. The display device 200 may be a computing device as known in the art, such as a smartphone, a laptop, a tablet computer, or the like. For example, the display device 200 may be an apparatus 102 as described above with respect to FIG. 1. The recording device 204 may be any device capable of capturing, monitoring, or generating waveform information as described above, such as an electrocardiograph or electroencephalograph. The recording device 204 is coupled to the patient 202 via a series of monitoring leads 206. The monitoring leads may each measure current at particular locations on the patient body. These changes in current may be stored as a particular waveform or as part of a set of waveform information. The recording device 204 may capture the waveform or set of waveform information. For example, the recording device 204 may include a storage medium to store the waveform or set of waveform information in non-volatile storage for later review and analysis. This stored information may later be accessed by a data management device 201 for viewing and analysis. Additionally or alternatively, the recording device 204 may communicate the waveform or set of waveform information to the data management device 201 during monitoring (e.g., in real-time). For example, the recording device 204 may communicate with the display device 200 via Bluetooth®, Wi-Fi, or the like. The data management device 201 may store and provide data to the display device 200 in a format suitable for output via the display device 202. For example, the display device 200 may include one or more interfaces for interacting with and/or configuring the data management device 201 (e.g., beginning and ending monitoring operations). In some embodiments, the display device 200 may also include an interface for selecting particular waveforms for display, such as an interface for interacting with stored patient medical records, an interface for connecting to a particular recording device 204, and the like. Although the instant example is provided with respect to separate structures for a display device 200, a data management device 201, and a recording device 204, it should be appreciated that various functions could be combined into a single device, such as a display device 200 that also performs the functionality of a data management device 201, a recording device 204 that also interfaces with a display device as a data management device 201, a single device that monitors leads, stores waveform data, and displays the waveform data, or any other combination of devices.

Example Interface Illustrations

FIG. 3 is an illustration of an example interface 300 for displaying a waveform. The interface 300 illustrates an example waveform, such as a waveform corresponding to a lead of an electrocardiograph monitor. For example, the interface 300 is depicting a waveform provided by a "V2" lead of an electrocardiograph. The interface 300 may be displayed, for example, on a display device coupled to a tablet computer, smartphone, desktop, laptop, or the like. Input may be provided to the interface via various input devices, including but not limited to a touch screen display, a mouse cursor, a keyboard, a gesture sensor, or the like.

FIG. 4 is an illustration of an example interface 400 depicting the use of an interface control for selecting a portion of a displayed waveform. The interface 400 depicts a waveform 402 and an interface control 404 for selecting a portion of the waveform 402. The interface control 404 includes a vertical selection control 406, a horizontal selection control 408, and a lock control 412.

The vertical selection control 406 may be used to define a vertical selection range, and/or to measure a vertical portion of the waveform. For example, the vertical selection control 406 may be used to measure an amplitude of the waveform. The horizontal selection control 408 may be used to define a horizontal selection range, and/or to measure a horizontal portion of the waveform. For example, the horizontal selection control 408 may be utilized to measure a time interval of the waveform based on the width of the horizontal selection control 408. In some embodiments, the vertical selection control 406 and the horizontal selection control 408 may be manipulated via a touch input provided via the interface. For example, the width of the vertical selection control 406 and the horizontal selection control 408 may be adjusted by performing a "pinch" input operation on each selection control on a touch screen interface.

A user may provide input to manipulate the horizontal selection control 406 and/or the vertical selection control 408 to select a portion of the waveform 402. For example, the user may define a vertical range and/or a horizontal range of the waveform 402 to be captured for display on the interface control 404. Although the instant example is described with respect to selection of both a vertical range and a horizontal range, it should be appreciated that some embodiments may only require selection of a horizontal range defining the beginning portion and ending portion of the waveform 402 for selection. For example, the horizontal range may be defined such that a single "beat" of the waveform is selected. The lock control 412 may be used to "lock" the horizontal selection control 406 and/or the vertical selection control 408. Upon locking the interface control 404, touch input provided on a portion of the screen corresponding to the interface control 404 may slide the interface control along with a display of the selected portion of the waveform. In contrast, if the interface control 404 is not locked, then touch input provided on a portion of the screen corresponding to the interface control 404 may adjust the horizontal and/or vertical interface controls to select a different portion of the waveform.

FIG. 5 is an illustration of an example interface 500 depicting the use of an interface control to capture a selected portion of a first waveform 504 with a second waveform 502. The interface 500 depicts the interface control as a portion of a waveform (e.g., the portion of the waveform selected via the interface 400 as described above) displayed on a semi-transparent "pane of glass" as part of an interface control. The second waveform 502 is visible through the "pane of glass" such that both the selected portion of the first waveform 504 and the second waveform 502 are visible.

The user may provide input 506 to scroll either the second waveform 502 or the portion of the first waveform 504 to align the portion of the first waveform 504 with the second waveform 502. For example, a "drag" operation to the left or right may scroll either the interface control or the second waveform 502 to the left or right. In this manner, the user may manipulate either the interface control or the second waveform 502 to align a selected portion of the first waveform with a corresponding portion of the second waveform (e.g., a first "beat" of each waveform). Display of the selected portion of the first waveform 504 and the second waveform 502 in this manner may allow for easy comparison between the two.

Although the instant example has been described with respect to a first waveform and a second waveform, it should be appreciated that the same or similar techniques could also be applied to compare within a waveform. For example, the interface control may allow for selection of a particular "beat" of the waveform, which may be captured into the interface control. The waveform or interface control may be scrolled to compare the selected beats with other beats of the waveform.

In some embodiments, the portion of the waveform selected by the interface control may be programmatically compared to the portion of the second waveform displayed underneath the interface control. For example, the interface may calculate the difference between differences in amplitude of the selected portion of the first waveform and the second waveform and display a measurement of the differences between corresponding portions of the two waveforms. Similarly, calculations may be made based on the horizontal measurements of each waveform, such as the duration of each heartbeat contained within the selected portions.

Example Method for Analyzing Waveform

FIG. 6 is a flow diagram of an example method 600 for analyzing a waveform using an interface control in accordance with embodiments of the present invention. The method 600 describes a process by which a portion of a waveform may be selected and captured using an interface control. The captured portion of the waveform may be displayed on a semi-transparent interface control for comparison with another waveform. Embodiments of the method 600 may be implemented using an apparatus, such as the interface 102 or display device 200 described above with respect to FIGS. 1 and 2.

At action 602, a waveform and an interface control are displayed. As described above with respect to the interface 400, the interface control may allow for selection of a portion of the waveform by adjusting a horizontal and/or vertical selection control. At action 604, an input is received selecting a portion of the waveform. For example, a user may define a horizontal range of the waveform for selection by adjusting one or both sides of a horizontal selection control. In some embodiments, an input may be further provided to confirm the selected portion of the waveform. For example, a user may adjust a horizontal selection component and then select a lock control to lock the selected portion of the waveform to the interface control. Upon selection of the lock control, scrolling of the waveform or the interface control may result in the selected portion of the waveform being captured to the interface control for comparison to another portion of the waveform or another waveform.

At action 606, a semi-transparent interface control is generated using the selected portion of the waveform. For example, as described above with respect to the interface 500, the selected portion of the waveform may be displayed on a semi-transparent glass control such that a different portion of the waveform or a second waveform is visible through the interface control. At action 608, an input is received to position the interface control. For example, an input may initiate a scrolling operation on the waveform or a scrolling operation on the interface control to align the interface control with a particular portion of the waveform. Additionally or alternatively, input may be received to review a different waveform while maintaining the selected portion of the original waveform on the interface control. For example, a user may capture a portion of a first waveform to an interface control, and select a second waveform for display, then align the interface control with a portion of the second waveform to compare the selected portion of the first waveform with a selected portion of the second waveform. In this manner, users may be provided with the ability to perform a direct comparison between portions of waveforms to easily visually identify differences and similarities.

It will be understood that each element of the flowchart, and combinations of elements in the flowchart, may be implemented by various means, such as hardware, firmware, processor, circuitry, and/or other devices associated with execution of software including one or more computer program instructions. For example, one or more of the procedures described above may be embodied by computer program instructions. In this regard, the computer program instructions which embody the procedures described above may be stored by a memory 104 of an apparatus employing an embodiment of the present invention and executed by a processor 102 of the apparatus. As will be appreciated, any such computer program instructions may be loaded onto a computer or other programmable apparatus (e.g., hardware) to produce a machine, such that the resulting computer or other programmable apparatus implements the functions specified in the flowchart blocks. These computer program instructions may also be stored in a computer-readable memory that may direct a computer or other programmable apparatus to function in a particular manner, such that the instructions stored in the computer-readable memory produce an article of manufacture the execution of which implements the function specified in the flowchart blocks. The computer program instructions may also be loaded onto a computer or other programmable apparatus to cause a series of operations to be performed on the computer or other programmable apparatus to produce a computer-implemented process such that the instructions which execute on the computer or other programmable apparatus provide operations for implementing the functions specified in the flowchart blocks.

Accordingly, blocks of the flowchart support combinations of means for performing the specified functions and combinations of operations for performing the specified functions for performing the specified functions. It will also be understood that one or more blocks of the flowchart, and combinations of blocks in the flowchart, can be implemented by special purpose hardware-based computer systems which perform the specified functions, or combinations of special purpose hardware and computer instructions.

In some embodiments, certain ones of the operations above may be modified or further amplified. Furthermore, in some embodiments, additional optional operations may be included. Modifications, additions, or amplifications to the operations above may be performed in any order and in any combination.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

That which is claimed:

1. A method comprising:
    displaying a first waveform in a user interface;
    generating, using a processor, an interface control, wherein the interface control comprises a vertical selection control and a horizontal selection control;
    receiving an input via the vertical selection control and horizontal selection control of the interface control selecting a portion of the first waveform;
    generating, using a processor, a semi-transparent display area and the selected portion of the first waveform displayed on the semi-transparent display area; and
    displaying the interface control comprising the semi-transparent display area concurrently with a second waveform such that at least a portion of the second waveform is visible through the semi-transparent display area of the interface control, wherein the interface control comprises a lock control movable between a locked and an unlocked setting, the method further comprising:
        changing the selected portion of the first waveform in the horizontal direction in response to user input in the horizontal direction with the lock control being in the unlocked setting; and
        translationally changing the position of the semi-transparent display area comprising the selected portion of the first waveform in response to user input in the horizontal direction with the lock control being in the locked setting.

2. The method of claim 1, wherein the second waveform is a different portion of the first waveform from the selected portion of the first waveform.

3. The method of claim 1, wherein the input selecting a portion of the first waveform comprises defining a horizontal range of the waveform using the horizontal selection control.

4. The method of claim 1, wherein the input selecting a portion of the first waveform comprises defining a vertical range of the waveform using the vertical selection control.

5. The method of claim 1, wherein the second waveform is a different waveform from the first waveform.

6. The method of claim 1, wherein the selected portion of the first waveform is displayed as an opaque line on the semi-transparent display area.

7. The method of claim 1, further comprising:
    receiving a scroll input corresponding to the second waveform; and
    in response to receiving the scroll input, aligning the second waveform with the interface control.

8. The method of claim 1, further comprising:
    receiving a scroll input corresponding to the interface control; and
    in response to receiving the scroll input, aligning the interface control with at least a portion of the second waveform.

9. The method of claim 1, wherein the first waveform is an electrocardiogram waveform.

10. The method of claim 1, wherein the selected portion of the first waveform corresponds to a beat of an electrocardiograph readout.

11. An apparatus comprising processing circuitry configured to cause the apparatus to:
    display a first waveform in a user interface;
    generate an interface control, wherein the interface control comprises a vertical selection control and a horizontal selection control;
    receive an input via the interface control selecting a portion of the first waveform;
    generate a semi-transparent display area and the selected portion of the first waveform displayed on the semi-transparent display area; and
    display the interface control comprising the semi-transparent display area concurrently with a second waveform such that at least a portion of the second waveform is visible through the semi-transparent display area of the interface control, wherein the interface control comprises a lock control movable between a locked and an unlocked setting, the apparatus further configured to:
- change the selected portion of the first waveform in the horizontal direction in response to user input in the horizontal direction with the lock control being in the unlocked setting; and
- change the position of the semi-transparent display area comprising the selected portion of the first waveform relative to the second waveform in response to user input in the horizontal direction with the lock control being in the locked setting.

12. The apparatus of claim 11, wherein the second waveform is a different portion of the first waveform from the selected portion of the first waveform.

13. The apparatus of claim 11, wherein the second waveform is a different waveform from the first waveform.

14. The apparatus of claim 11, further caused to:
- receive a scroll input corresponding to the second waveform; and
- in response to receiving the scroll input, align the second waveform with the interface control.

15. The apparatus of claim 11, further caused to:
- receive a scroll input corresponding to the interface control; and
- in response to receiving the scroll input, align the interface control with at least a portion of the second waveform.

16. A computer program product comprising at least one computer-readable storage medium bearing computer program instructions embodied therein for use with a computer, the computer program instructions comprising program instructions configured to:
- display a first waveform;
- generate an interface control, wherein the interface control comprises a vertical selection control and a horizontal selection control;
- receive an input via the vertical selection control and horizontal selection control of the interface control selecting a portion of the first waveform;
- generate a semi-transparent display area and the selected portion of the first waveform is displayed on the semi-transparent display area; and
- display the interface control comprising the semi-transparent display area concurrently with a second waveform such that at least a portion of the second waveform is visible through the semi-transparent display area of the interface control, wherein the interface control comprises a lock control movable between a locked and an unlocked setting, the program code instructions further configured to:
  - change the selected portion of the first waveform in the horizontal direction in response to user input in the horizontal direction with the lock control being in the unlocked setting; and
  - change the position of the semi-transparent display area comprising the selected portion of the first waveform relative to the second waveform in response to user input in the horizontal direction with the lock control being in the locked setting.

17. The computer program product of claim 16, wherein the second waveform is a different portion of the first waveform from the selected portion of the first waveform.

18. The computer program product of claim 16, wherein the second waveform is a different waveform from the first waveform.

19. The method of claim 1, further comprising:
- changing a vertical selection range of the first waveform in response to user input in the vertical direction with the lock control being in the unlocked setting, and
- changing the position of the semi-transparent display area comprising the selected portion of the first waveform in response to user input in the vertical direction with the lock control being in the locked setting.

* * * * *